United States Patent [19]

Warawa

[11] Patent Number: 4,904,651
[45] Date of Patent: Feb. 27, 1990

[54] ANXIOLYTIC 4-AMINOQUINOLINE-3-CARBOXAMIDES

[75] Inventor: Edward J. Warawa, Wilmington, Del.

[73] Assignee: ICI Americas Inc., Wilmington, Del.

[21] Appl. No.: 227,761

[22] Filed: Aug. 3, 1988

Related U.S. Application Data

[63] Continuation of Ser. No. 43,843, Apr. 29, 1987, abandoned.

[30] Foreign Application Priority Data

May 6, 1986 [GB] United Kingdom ................ 8610981

[51] Int. Cl.$^4$ .................... A61K 31/47; C07D 215/54; C07D 401/02; C07D 401/14
[52] U.S. Cl. .................... 514/183; 514/212; 514/313; 540/481; 540/597; 546/156; 546/159; 546/170; 560/43
[58] Field of Search ........................ 514/212, 313, 183; 540/481, 597; 546/159

[56] References Cited

U.S. PATENT DOCUMENTS

| | | | |
|---|---|---|---|
| 3,362,954 | 1/1968 | Surrey et al. | 544/80 |
| 4,450,167 | 5/1984 | Le Martret et al. | 546/159 |
| 4,511,568 | 4/1985 | Bare et al. | 514/293 |
| 4,546,104 | 10/1985 | Campbell et al. | 514/293 |
| 4,552,883 | 11/1985 | Bare | 514/303 |
| 4,705,793 | 11/1987 | Resch | 514/293 |
| 4,745,121 | 5/1988 | Bare | 514/293 |
| 4,788,188 | 11/1988 | Vernieres et al. | 514/313 |
| 4,789,678 | 12/1988 | Effland et al. | 546/159 |
| 4,806,549 | 2/1989 | Ife et al. | 546/159 |

FOREIGN PATENT DOCUMENTS 2581382 11/1986 France .
2047244 11/1980 United Kingdom .

OTHER PUBLICATIONS

Patel et al., *Pharmac. Biochem. Behav.* 12 p. 819 (1980).
Sen et al., *Jour. Indian Chem. Soc.* 42, p. 851 (1965).
Bala et al., *Chemical Abstracts,* vol. 106, No. 176143 (1987).
Bala et al., *Current Abstracts of Chemistry,* vol. 102, No. 391634 (1986).
Sen et al., Chemical Abstracts, vol 64, 14164b (1966).
Schäfer et al., *Monatsh. Chem.* 109 pp. 527–535 (1978).
Derwent Abstract No. 86-333948/51 for Fr Patent No. 2581382 (11/7/86).

Primary Examiner—Mukund J. Shah
Assistant Examiner—E. Bernhardt
Attorney, Agent, or Firm—Rosemary M. Miano; Thomas E. Jackson

[57] ABSTRACT

The present invention comprises certain amide derivatives of 4,8-disubstituted quinoline-3-carboxylic acids of formula I; pharmaceutically acceptable salts of the compounds of formula I; pharmaceutical compositions containing a compound of formula I, or a pharmaceutically acceptable salt thereof, for use in the treatment of anxiety; and processes for the manufacture of the compounds of formula I, as well as intermediates for use in such manufacture.

8 Claims, No Drawings

ANXIOLYTIC 4-AMINOQUINOLINE-3-CARBOXAMIDES

This application is a continuing application of an application with Ser. No. 07/043,843, filed April 29, 1987 and now abandoned.

SUMMARY OF THE INVENTION

The compounds of the invention are 4-aminoquinoline-3-carboxamides which are useful as agents for binding to benzodiazapine receptors, and which may also be useful as biochemical tools.

DETAILED DESCRIPTION OF THE INVENTION

The compounds of the invention are 4-aminoquinoline-3-carboxamides of formula I:

(Formula set out on pages following Examples) I
where
Ra is selected from the group consisting of (1–10C)alkyl, (3–10C)cycloalkyl, (4–10C)cycloalkylalkyl, (2–10C)alkenyl, (2–10C)alkynyl, (6–10C)aryl, (7–12C)arylalkyl, (1–10C)haloalkyl having at least one halo group wherein the halo group(s) is selected from chloro and fluoro, (2–10C)hydroxyalkyl, (4–10C)hydroxycycloalkylalkyl, and heteroaryl having a 5 or 6-membered ring and having one or more heteroatoms selected from sulfur, oxygen and nitrogen, wherein the heteroaryl is optionally substituted by (1–5C)alkyl;

Rb and Rc may be the same or different and are each independently selected from the group consisting of hydrogen, (1–10C)alkyl, (3–10C)cycloalkyl, (4–10C)cycloalkylalkyl, (2–10C)alkenyl, (2–10C)alkynyl, (2–10C)alkoxyalkyl, (2–10C)hydroxyalkyl, (3–10C)hydroxycycloalkyl, (4–10C)hydroxycycloalkylalkyl, (2–10C)haloalkyl having at least one halo group (wherein the halo group(s) is selected from chloro and fluoro), (3–6C)haloalkenyl having at least one halo group (wherein the halo group is selected from chloro and fluoro), phenyl and benzyl;

or Rb and Rc taken together form a (3–10C)alkylene and together with the nitrogen to which they are attached form a ring;

Rd is selected from the group consisting of hydrogen, (1–6C)alkyl and (1–6C)alkanoyl; and the pharmaceutically acceptable acid addition salts thereof.

Particular values for Ra are (2–6C)alkyl, (3–7C)cycloalkyl, (4–7C)cycloalkylalkyl, (3–6C)alkenyl, (3–6C)alkynyl, (6–10C)aryl, benzyl, (3–6C)haloalkyl, (3–6C)hydroxyalkyl, (4–7C)hydroxycycloalkylalkyl, and 3-methyl-2-thienyl.

Particular values for Rb and Rc are hydrogen, (2–6C)alkyl, (3–7C)cycloalkyl, (4–7C)cycloalkylalkyl, (3–6C)alkenyl, (3–6C)alkynyl, (2–6C)alkoxyalkyl, (2–6C)haloalkyl, and (3–6C)haloalkenyl where the halo group(s) is on a carbon having a double bond.

Particular values for Rd are hydrogen, (2–4C)alkanoyl such as acetyl, propionyl and butyryl.

More particular values for the above defined groups are as follows:

Ra: ethyl, propyl, butyl, pentyl, 3-pentynyl and 2-methylpropyl;

Rb: propyl, 2-propenyl, cyclopropylmethyl, 2,2,2-trifluoroethyl, 2-chloro-2-propenyl, and 3,3-dichloro-2-propenyl;

Rc: hydrogen; and

Rd: hydrogen.

A particular pharmaceutically acceptable acid addition salt is one formed with hydrochloric, hydrobromic, sulfuric, nitric, phosphoric or an alkane sulfonic acid such as methanesulfonic acid.

The salts of the compounds of formula I are preferably the pharmaceutically acceptable salts, but other salts may, for example, find use in the preparation of the compounds of formula I and the pharmaceutically acceptable salts thereof.

Preferred compounds of the invention in order of preference are (a) 4-amino-8-butylquinoline-3-[N-(2-propenyl)]carboxamide (Example 7); and (b) 4-amino-8-butylquinoline-3-[N-propyl]carboxamide (Example 6).

It will be appreciated that certain of the compounds of this invention may contain an asymmetrically substituted carbon atom and may exist in, and be isolated in, optically-active and racemic forms. In addition, it will be appreciated that certain compounds of this invention may contain a double bond and may exist in, and be isolated in, separate stereoisomeric forms ('E' and 'Z') about that group. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses the utilities described herein, it being well known in the art how to prepare optically-active forms (for example, by resolution of the racemic form or by synthesis from optically-active starting materials) and individual 'E' and 'Z' stereoisomers (for example, by chromatographic separation of a mixture thereof) and how to determine the properties described herein by the standard tests described hereinafter.

In this specification Ra, Rb, Rc, Rd, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, "alkylene" and "alkenylene" et cetera. Halogeno is fluoro, chloro, bromo or iodo.

Compounds of formula I may be prepared using methods known for the preparation of chemically similar compounds. Thus the following processes are provided as further features of the invention where Ra, Rb, Rc and Rd have the definitions stated above unless indicated otherwise:

(a) reaction of a compound of formula II:

(Formula set out on pages following Examples) II
where A is a carboxylic acid (—COOH) or activated derivative thereof, for example ester, acid chloride (preferred), acid anhydride or acyl imidazolide, with an amine of formula RbRcNH;

(b) reaction of a compound of formula IIa:

(Formula set out on pages following Examples) IIa
where $A^1$ is an ester having 1–6 carbons (for example, —$CO_2CH_2CH_3$ or —$CO_2CH_3$), with an aluminum reagent of the formula $Re_2AlNRbRc$ or $ReAl(Cl)NRbRc$ wherein Re is methyl, ethyl, propyl, or isobutyl;

(c) reaction of a compound of formula III:

(Formula set out on pages following Examples) III
where X is iodo or bromo, with an organometallic reagent of formula RaMX or $Ra_2M$, wherein M is magnesium or zinc, in the presence of a palladium catalyst (for example, dichloro[1,1'-bis(diphenylphosphino)ferrocene]palladium (II)).

(d) for a compound of formula I in which Rd is alkanoyl, acylation of a corresponding compound of formula I in which Rd is hydrogen.

Both processes (a) and (b) are preferred methods. Process (b) is based in part on the work of S. M. Weinreb, et al., *Synthetic Communications*, (1982) 12: 989–993, which describes direct conversion of esters to carboxamides employing aluminum amide reagents.

The starting material for processes (a) and (b) may be prepared from a compound of formula IV:

(Formula set out on pages following Examples) IV where $A^1$ has the value as defined above, by first converting the hydroxyl group to a suitable leaving group, examples being chloro, bromo and ethoxy, followed by displacement with an amine of formula $RdNH_2$ to give a compound of formula IIa. Either direct conversion to compounds of formula I by process (b) or conversion to the acid by hydrolysis of the ester to then use process (a) can be accomplished.

The starting material of formula IV where $A^1$ is $-CO_2CH_2CH_3$ or $-CO_2CH_3$ may be formed according to the procedure of R. G. Gould et al., *J. Amer. Chem. Soc.*, (1939) 61: 2890–2895 which describes the synthesis of such components from anilines. For the processes of this invention the use of ortho-substituted anilines give the desired compounds.

All of the anilines used in the examples were commercially available except for 2-pentylaniline and 2-butylaniline. 2-Pentylaniline and 2-butylaniline may be made by methods well documented in the literature, for example see P. G. Gassman et al., *J. Amer. Chem. Soc.*, (1974) 96: 5487-95; and R. Sikkar et al. *Acta Chemica Scandinavica*, (1980) Vol. B34, pp. 551-557 respectively.

For process (c) a compound of formula IIb:
(Formula set out on pages following Examples) IIb where $A^1$ has a value as defined above and X is iodo or bromo, may be converted to the corresponding carboxamide of formula III according to the procedure of process (b) using the aluminum amide reagents. Subsequent organometallic cross-coupling then may be achieved by process (c) paralleling the chemistry of T. Hayashi et al., *J. Amer. Chem. Soc.*, (1984) 106: 158–163. Compounds of formula IIb may be made from corresponding ortho-haloanilines using the procedures described for formula IIa.

Pharmaceutically acceptable acid addition salts may be formed by reacting a compound of formula I with an appropriate acid, for example, by dissolving a compound of formula I, adding a selected acid to the solution and recovering the salt.

It may be desired to optionally use a protecting group during all or portions of the above described processes; the protecting group may then be removed at the appropriate time.

As indicated above, the compounds of the present invention are useful as binders to benzodiazepine receptors. This may be demonstrated by using a tritiated flunitrazepam assay (FNB test) (see U.S. Pat. Nos. 4,511,568 and 4,546,104.) Compounds capable of binding to benzodiazepine receptors are known to possess a spectrum of activities which range from anxiolytic activity to the activity of reversing the action of benzodiazepines in the central nervous system. In general, the compounds of the present invention are believed to possess anxiolytic activity. It will be appreciated, however, that compounds will vary in their activity depending on chemical structure and thus compounds of the present invention will possess a varying ratio of such above mentioned activities. Anxiolytic activity may be demonstrated in the Shock-Induced Suppression of Drinking (Rats) Test (SSD) described in *Pharmacology Biochemistry and Behaviour*, (1980) 12: 819–821. This test may be carried out as follows:

Male rats in the weight range of 200 to 220 g are deprived of water for 48 hours and deprived of food for 24 hours before testing. Normally, the rats are orally intubated and receive a volume of 5 ml/kg containing the appropriate concentration of test compound (based on mg/kg body weight). The vehicle control group of rats is also intubated by mouth. A positive control group of rats is also orally administered a control dose of 18 mg/kg of chlordiazepoxide. Random selection of the rats is utilized in dosing. The rats are returned to the cage for one hour. Sixty minutes after drug administration, the rat is quietly removed from its cage and the hind feet wiped with Signa electrode gel made by Parker Laboratories of Orange, New Jersey. When intraperitoneal (i.p.) administration is used, the protocol is identical except that the drugs are administered in varying concentrations in a volume of 5 ml/kg 30 minutes prior to testing. Concentrations ranged from 0.4 to 50 mg/kg. The rat is placed on the floor in the chamber facing the licking tube. The animal is allowed 5 minutes to make 20 licking responses and receive the first shock (0.5 mA). If this response does not occur, the animal is removed and eliminated from the study. If 20 licking responses are made, the animal is permitted an additional 3 minutes during which time each 20th lick is paired with a 0.5 mA shock. This period is automatically started, counted and terminated. The number of licks and shocks are recorded. The activity of the compound tested is evaluated by comparing the mean shocks of the group dosed with the test compound to both the mean shocks of the vehicle and positive control groups via a Students' t-test. In general, an increase in the number of shocks received compared to the control is indicative of the anti-conflict or anti-anxiety activity of the compound.

In general, no sign of overt toxicity has been observed with compounds of the invention at dosages at least several multiples of their minimum effective doses in the SSD Test.

Representative compounds of the present invention typically show results in the SSD test indicative of anxiolytic activity.

According to a further feature of the invention there is provided a pharmaceutical composition which comprises a quinoline carboxamide derivative of the invention in association with a pharmacetuically-acceptable diluent or carrier.

The pharmaceutical composition may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories or sterile injectable aqueous or oily solutions or suspensions.

A preferred pharmaceutical composition of the invention is one suitable for oral administration in unit dosage form, for example a tablet or capsule which contains between 0.1 mg and 500 mg of the quinoline carboxamide derivative, or one suitable for intravenous, intramuscular or subcutaneous injection; for example, a sterile injectable containing between 0.1% and 10% w/w of the quinoline carboxamide derivative.

The pharmaceutical composition of the invention will normally be administered to mammals such as man for relief of anxiety and tension in the same manner as that employed for chlordiazepoxide, due allowance being made in terms of dose levels for the potency and duration of actions of the quinoline carboxamide derivative of the invention relative to chlordiazepoxide. Thus each individual, will receive an oral dose of between 0.5 mg and 500 mg, and preferably between 0.5 mg and 20 mg, of quinoline carboxamide derivative, or an intravenous, subcutaneous or intramuscular dose of between 0.5 mg and 100 mg, and preferably between 0.5 mg and 20 mg, of the quinoline carboxamide derivative, the composition being administered one to four times per day. The rectal dose will be approximately the same as the oral dose.

The invention is illustrated but not limited by the following examples in which temperatures are in degrees Celsius, ambient temperature refers to 23±3. Chemical symbols have their usual meanings unless otherwise specified and the following abbreviations are used: ml (milliliter), g (gram), mg (milligram), m.p. (melting point), tlc (thin layer chromatography), $R_f$ (relative mobility in tlc), < (less than), > (greater than), atmospheric pressure ($1.013 \times 10^5$ Pascals/atm), hr. (hour), min. (minutes). Ra, Rb, Rc, Rd, and Re have the meanings defined above and have no other chemical significance unless otherwise noted. Unless otherwise stated, solvent ratios are by a volume/volume (v/v) basis.

EXAMPLE 1 a. 4-Amino-8-ethylquinoline-3-(N-propyl)carboxamide (Formula I, Ra=ethyl, Rb=propyl, Rc=Rd=hydrogen)

A mixture of the quinoline carboxylic acid (1.1 g) described in Example 1f and thionyl chloride (0.73 ml) was heated to reflux in methylene chloride (15 ml). After heating 96 hr, the mixture was cooled in an ice bath and propylamine (4 ml) added quickly. After stirring for a few minutes the volatiles were removed in vacuo and the residue partitioned between ethyl acetate and water. The layers were separated and the aqueous layer was extracted with two more portions of ethyl acetate. The combined organic layer was dried over $MgSO_4$ and concentrated to a solid residue (600 mg). Recrystallization from methylene chloride/hexane afforded the title compound as fine white needles with a m.p. of 166-167.5.

Analysis calculated for $C_{15}H_{19}N_3O$: C, 70.01; H, 7.44; N, 16.33. Found: C, 69.67; H, 7.44; N, 16.26.

b. Diethyl (2-ethylphenyl)aminomethylenemalonate

A mixture of 2-ethylaniline (11.7 g) and diethyl ethoxymethylene malonate (25.0 g) were warmed together at 80° C. for one hour. After cooling, the mixture was poured with stirring into a mixture of 150 ml of ether and 75 ml of hexane. After cooling the solution in an ice bath colorless needles precipitated and were collected by filtration. There was obtained 26.7 g (95%) of the title product; tlc, $R_f=0.73$, silica gel, ethyl acetate:hexane (1:1).

c. Ethyl 8-ethyl-4-hydroxyquinoline-3-carboxylate (Formula IV, Ra=ethyl, $A^1$=—$CO_2CH_2CH_3$)

A solution of the product described in Example 1b (26.7 g) in diphenyl ether (about 50 ml) was heated with stirring to 250° for 1.5 hr. After cooling to ambient temperature, ether (50 ml) was added and the precipitate filtered. The supernatant was concentrated to remove ether then reheated to 250° C. for an additional 1.5 hr. After cooling to ambient temperature and adding ether, an additional crop of material was obtained. There was obtained a total of 20.0 g (85%) of the crude product with a m.p. of 220°-230° C.

d. Ethyl 4-chloro-8-ethylquinoline-3-carboxylate

The hydroxyquinoline (8.0 g) described in Example 1c was combined with phosphoryl chloride (15 ml) followed by warming to 75° C. for 30 min. After cooling the residue was taken up in ethyl acetate (100 ml) and water (50 ml) was carefully added. Saturated aqueous sodium bicarbonate (45 ml) was added and the layers separated. The ethyl acetate layer was dried over $MgSO_4$ and concentrated to leave a viscous oil (8.13 g, 94%); tlc, $R_f=0.72$, silica gel, ethyl acetate:hexane (1:1).

e. Ethyl 4-amino-8-ethylquinoline-3-carboxylate (Formula IIa, Ra=ethyl, Rd=H, $A^1$=—$CO_2CH_2CH_3$)

The quinoline ester (8.13 g) from Example 1d was placed in a stainless steel pressure vessel and ethanol (50 ml), which had been cooled in an ice bath and saturated with ammonia, was added. The pressure vessel was sealed and heated to 100° C. for 9 hr. After cooling and filtering the mixture 6.4 g (85%) of the aminoquinoline was obtained as yellow needles with a m.p. of 188°-191° C.; tlc, $R_f=0.54$, silica gel, ethyl acetate:hexane (1:1).

f. 4-Amino-8-ethyl-3-quinoline carboxylic acid (Formula II, Ra=ethyl, Rd=H, A=—COOH)

A mixture of the aminoquinoline (24 g) described in Example 1e and methanol (100 ml) was treated with 10N KOH (40 ml, aqueous). The resulting mixture was stirred for 12 hr. at ambient temperature. The mixture was cooled and partitioned between water (100 ml) and ether (50 ml). The ether layer was separated and the aqueous phase acidified with glacial acetic acid. The precipitate was filtered off and dried overnight under high vacuum to afford the acid (14.0 g, 76%) as a white powder with a m.p. >250° C.

EXAMPLE 2

4-Amino-8-propylquinoline-3-(N-propyl)carboxamide (Formula I, Ra=propyl, Rb=propyl, Rc=Rd=hydrogen)

The processes described in Examples 1b-1f were repeated using 2-propylaniline instead of 2-ethylaniline in Example 1b to afford the quinoline carboxylic acid of Formula II (Ra=propyl, Rd=hydrogen, A=—COOH). Then a procedure similar to that described for Example 1a was followed except the quinoline carboxylic acid (1.1 g) was reacted with thionyl chloride (1.2 ml) in methylene chloride (100 ml). After heating for 96 hr. and quenching with propylamine (10 ml) at 0° C., the crude product was isolated as described in Example 1a. Recrystallization from chloroform/hexane gave the title compound as a white solid (0.83 g, 64%) with a m.p. of 118°–119°; tlc, $R_f$=0.32, silica gel, ethyl acetate:hexane (2:3).

Analysis calculated for $C_{16}H_{21}N_3O$: C, 70.82; H, 7.80; N, 15.49. Found: C, 70.93; H, 8.07; N, 15.39.

EXAMPLE 3

4-Amino-8-propylquinoline-3-[N-(2-propenyl)]carboxamide (Formula I, Ra=propyl, Rb=2-propenyl, Rc=Rd=hydrogen)

The procedure described in Example 2 down to the formation of the quinoline carboxylic acid (1.8 g) was repeated using the methods described in Examples 1b–1f. The quinoline carboxylic acid (1.8 g) was reacted as described in Example 2 (1.8 g) with thionyl chloride (1.2 ml) in methylene chloride (100 ml). After heating for 96 hr. the mixture was cooled to 0° and quenched with 2-propenylamine (10 ml). The crude product was isolated as described in Example 1a. The residue was recrystallized from chloroform/hexane to give a white solid (0.68 g, 32%) with a m.p. of 125°–126°; tlc, $R_f$=0.38, silica gel, ethyl acetate:hexane (2:3).

Analysis calculated for $C_{16}H_{19}N_3O$: C, 71.35; H, 7.11; N, 15.60. Found: C, 71.00; H, 7.30; N, 15.46.

EXAMPLE 4

4-Amino-8-pentylquinoline-3-(N-propyl)carboxamide (Formula I, Ra=pentyl, Rb=propyl, Rc=Rd=hydrogen)

The processes described in Examples 1b–1f were repeated using 2-pentylaniline (3.38 g) in Example 1b instead of 2-ethylaniline. A quinoline carboxylic acid of the formula II (Ra=pentyl, Rd=H, A=COOH) was obtained. To a mixture of this quinoline carboxylic acid (0.50 g) and chloroform (10 ml) was added thionyl chloride (0.42 ml). After stirring for 2.5 hr. at ambient temperature the mixture was cooled to 0° and propylamine (1.90 ml) was added all at once. The clear, yellow solution was stirred for 15 min and then poured, with stirring, into water. Additional chloroform was added and the layers were separated. The chloroform layer was washed with water, then dried over $MgSO_4$. After concentrating the material there was obtained 0.48 g of a yellow solid. The crude solid was dissolved in methylene chloride and chromatographed over silica gel using methanol:methylene chloride (1:24) as the eluent. The resulting solid was recrystallized from petroleum ether to give the title compound (0.34 g, 59%) as a white solid, with a m.p. of 138.5°–140.5°; tlc, $R_f$=0.70, silica gel, methanol:methylene chloride (2:23).

Analysis calculated for $C_{18}H_{25}N_3O$: C, 72.20; H, 8.42; N, 14.03. Found: C, 71.99; H, 8.31; N, 13.99.

EXAMPLE 5

4-Amino-8-pentylquinoline-3-[N-(2-propenyl)]carboxamide (Formula I, Ra=pentyl, Rb=2-propenyl, Rc=Rd=hydrogen)

The procedures of Examples 1b–1f were followed to obtain the quinoline carboxylic acid except that 2-pentylaniline (3.38 g) was used instead of 2-ethylaniline and was reacted with 4.48 g of diethylethoxymethylenemalonate to obtain a compound of formula II (3.52 g, 66%) (Ra=pentyl, Rd=H, A=—COOH). Then, using this quinoline carboxylic acid (0.95 g), a procedure similar to that described in Example 4 was followed except that the quinoline carboxylic acid was reacted with thionyl chloride (0.40 ml) in chloroform (9.5 ml), followed by reaction with 2-propenylamine (1.48 ml). After work-up of the reaction mixture as described in Example 4 the crude product was chromatographed over silica gel using methanol/methylene chloride (1:24) as the eluent. There was obtained a yellow solid (0.44 g, 40%). Recrystallization from petroleum ether gave a white solid, m.p. 127.5°–128.5°; tlc, $R_f$=0.32, silica gel, methanol:methylene chloride (1:24).

Analysis calculated for $C_{18}H_{23}N_3O$: C, 72.69; H, 7.79; N, 14.13. Found: C, 72.69; H, 7.86; N, 14.08.

EXAMPLE 6

4-Amino-8-butylquinoline-3-(N-propyl)carboxamide (Formula I, Ra=butyl, Rb=propyl, Rc=Rd=hydrogen)

The processes described in Examples 1b–1e were repeated using 2-butylaniline (2.26 g) in Example 1b instead of 2-ethylaniline. A quinoline ester of formula IIa (Ra=butyl, Rd=H, $A^1$=—$COOCH_2CH_3$) was obtained. Then to a 0° C. suspension of propylamine hydrochloride (0.96 g) in toluene was added dropwise a 2.3M solution of trimethylaluminum (4.35 ml) in hexane. Following the addition the mixture was warmed to ambient temperature and stirred for 1 hr during which time the suspended amine hydrochloride was consumed. The resulting solution was cooled to 0° and the quinoline ester (1.09 g) was added quickly under a blanket of nitrogen. The mixture was heated to 100° and stirred for 2 hr. After cooling, the mixture was carefully quenched with aqueous hydrochloric acid and the mixture extracted with both ethyl acetate and $CH_2Cl_2$. The combined extracts were dried ($MgSO_4$) and concentrated to leave a crude solid. Purification by column chromatography over silica gel eluting with ethyl acetate/hexane (2:3) afforded a white solid. Recrystallization from $CH_2Cl_2$/hexane gave 0.90 g (79%) of the title compound, m.p. 128°–129°.

Analysis calculated for $C_{17}H_{23}N_3O$: C, 71.55; H, 8.12; N, 14.72. Found: C, 71.23; H, 7.89; N, 14.69.

EXAMPLE 7

4-Amino-8-butylquinoline-3-[N-(2-propenyl)]carboxamide (Formula I, Ra=butyl, Rb=2-propenyl, Rc=Rd=hydrogen)

A procedure similar to that described in Example 6 was followed except that 1.1 g of the quinoline ester was used, 4.3 ml of trimethylaluminum was used, and 2-propenylamine hydrochloride (0.98 g) was used in place of propylamine hydrochloride. After work-up the crude product was purified by chromatographing it over silica gel using ethyl acetate:hexane (3:7) as the eluent. The purified solid was recrystallized from methylene chloride/hexane to give fine, white crystals (0.63 g, 75%) with a m.p. of 126°–127°; tlc, $R_f$=0.35, silica gel, ethyl acetate:hexane (2:3).

Analysis calculated for $C_{17}H_{21}N_3O$: C, 72.05; H, 7.47; N, 14.83. Found: C, 71.93; H, 7.50; N, 14.82.

EXAMPLES 8–11

The process of Example 6 was repeated using the quinoline ester prepared using the process described in Examples 1b–1e using 2-propylaniline instead of 2-ethylaniline (formula IIa, Ra=propyl, Rd=H, $A^1$=

COOCH$_2$CH$_3$) and the appropriate amine hydrochloride of formula RbNH$_3$Cl with Rb having the value listed in Table I. Thus quinoline amides of formula I were obtained where Ra=propyl, Rc=Rd=H and Rb has the value listed in Table I for the particular example. These compounds and their physical data are listed in Table I.

all at once under a back-flush of argon. The mixture was stirred at ambient temperature for 18 hr. followed by cooling in an ice bath and quenching slowly with saturated aqueous NH$_4$Cl. The mixture was partitioned between ethyl acetate and excess water and the layers separated. The organic layer was washed with brine, dried over Na$_2$SO$_4$ and concentrated. Purification by

TABLE I

| Example | Rb | Yield | m.p. | Elemental Analysis Calculated | Found |
|---|---|---|---|---|---|
| 8* | Cyclopropylmethyl | 77% | 124–127° | C, 72.05; H, 7.47; N, 14.83 | C, 71.94; H, 7.35; N, 14.67 |
| 9 | 2,2,2-trifluoroethyl | 76% | 167–170° | C, 57.87; H, 5.18; N, 13.50 | C, 57.67; H, 5.12; N, 13.54 |
| 10 | 2-chloro-2-propenyl | 58% | 137–139° | C, 63.26; H, 5.97; N, 13.83 | C, 62.95; H, 5.83; N, 13.78 |
| 11* | 3,3-dichloro-2-propenyl | 80% | 164–167° | C, 56.81; H, 5.07; N, 12.42 | C, 56.93; H, 5.10; N, 12.38 |

*Single Analysis

EXAMPLE 12 a.
4-Amino-8-(3-pentynyl)quinoline-3-(N-propyl)carboxamide (Formula I, Ra=3-pentynyl, Rb=propyl, Rc=Rd=hydrogen)

A procedure similar to that described in Example 6 was followed except the quinoline ester product from Example 12b (0.50 g) was reacted with the reagent prepared by reaction of propylamine hydrochloride (0.15 g) with 0.68 ml of a 2.35M solution of trimethylaluminum in hexane. After recovery of the crude product as described in Example 6, a column was run over silica gel eluting with ethyl acetate:hexane (1:3) to give a white solid. Recrystallization from tert-butylmethyl ether/hexane gave the title compound (0.39 g, 75%) as a flocculent white solid, with a m.p. of 144°–145°; tlc, R$_f$=0.25: silica gel, ethyl acetate:hexane (1:3).

Analysis calculated for C$_{18}$H$_{21}$N$_3$O: C, 73.19; H, 7.17; N, 14.22. Found: C, 73.77; H, 7.22; N, 14.26.

b. Ethyl 4-Amino-8-(3-pentynyl)quinoline-3-carboxylate (Formula IIa, Ra=3-pentynyl, Rd=H, A$^1$=—COOCH$_2$CH$_3$)

The processes described in Examples 1b–1e were repeated using 2-iodoaniline (3.54 g) instead of the 2-ethylaniline used in Example 1b; the 2-iodoaniline was reacted with 3.56 g of diethylethoxymethylenemalonate to prepare a quinoline ester of the formula IIb (2.35 g, 42%) where X=iodo, A$^1$=COOCH$_2$CH$_3$ and Rd=hydrogen. The Grignard reagent was prepared by slow addition of 1-bromo-3-pentyne (13 g) to a 0° suspension of magnesium turnings (2.42 g) in dry tetrahydrofuran (60 ml) under an argon atmosphere. After stirring for 2 hr. at 0°, the mixture was warmed to ambient temperature and stirred for 15 min. The unreacted magnesium was allowed to settle and the supernatant transferred via cannula to a second flask containing anhydrous zinc bromide dissolved in tetrahydrofuran (25 ml). A mechanical stirrer was used to efficiently mix the resulting thick white precipitate. Following the transfer, the mixture was stirred 15 min. at ambient temperature followed by the addition of catalytic dichloro[1,1′-bis(diphenylphosphino)ferrocene]palladium (II) (0.30 g). After stirring a few minutes, the quinoline ester obtained by the method of Example 1e (3.46 g) was added column chromatography over silica gel eluting with ethyl acetate:hexane (1:4) afforded the desired product as a yellow solid (1.42 g, 50%); tlc, R$_f$=0.32: silica gel, ethyl acetate:hexane (1:3).

EXAMPLE 13 a.
4-Amino-8-(2-methylpropyl)quinoline-3-(N-propyl)carboxamide (Formula I, Ra=2-methylpropyl, Rb=propyl, Rc=Rd=hydrogen)

A procedure similar to that described in Example 12 for the formation of the quinoline ester was followed using the quinoline described in Example 13b (0.5 g), commercially available 2-methylpropylmagnesium bromide (7.3 ml of a 2.0M solution in ether) and 3.19 g of anhydrous zinc bromide. After completion of the reaction the crude product was isolated as described previously in Example 12a. Purification by column chromatography over silica gel using ethyl acetate:hexane as the eluent gave a white solid. Recrystallization from tert-butylmethyl ether/hexane gave a tan solid (0.17 g, 43%) with a m.p. of 138°–140°; tlc, R$_f$=0.36: silica gel, ethyl acetate:hexane (2:3).

b. 4-Amino-8-iodoquinoline-3-(N-propyl)carboxamide (Formula III, X=iodo, Rb=propyl, Rc=Rd=hydrogen)

A procedure similar to that described in Example 6 for the formation of the quinoline ester was followed using the quinoline described in Example 12b (4.0 g), propylamine hydrochloride (2.3 g) and trimethylaluminum (10 ml of a 2.35M solution in hexane). After isolation of the crude product as described in Example 6, the material was purified by column chromatography over silica gel using ethyl acetate:hexane (1:1) as the eluent. There was obtained 3.85 g (93%) of a cakey solid, m.p. 214°°–215°; R$_f$=0.27: silica gel, ethyl acetate:hexane (2:3).

Analysis calculated for C$_{17}$H$_{23}$N$_3$O: C, 71.55; H, 8.12; N, 14.72. Found: C, 71.22; H, 8.35; N, 14.46.

EXAMPLE 14

The following illustrates representative pharmaceutical dosage forms which may be used for the therapeutic or prophylactic administration of a compound of formula I or of a pharmaceutically acceptable salt thereof (hereinafter referred to as 'Compound A'):

| a. Tablet 1 | mg/tablet |
|---|---|
| 'Compound A' | 5 |
| Lactose | 88 |
| Magnesium stearate | 1 |
| Polyvinylpyrrolidone | 2 |
| Sodium starch glycollate | 4 |

The lactose, sodium starch glycollate and polyvinylpyrrolidone are mixed in a planetary mixer and water added until a suitable mass for granulation is obtained. The mass obtained is granulated through a suitable size mesh and dried to obtain the optimum moisture content. The magnesium stearate is then added and the dry granulate is then passed through a further screen before final blending and compression to yield tablets each weighing 100 mg.

| b. Tablet 2 | mg/tablet |
|---|---|
| 'Compound A' | 250 |
| Lactose | 122 |
| Magnesium stearate | 4 |
| Polyvinylpyrrolidone | 8 |
| Sodium starch glycollate | 16 |

The tablets are formulated as described in part a. to yield tablets each weighing 400 mg.

| c. Tablet 3 | mg/tablet |
|---|---|
| 'Compound A' | 100 |
| Lactose | 86 |
| Magnesium stearate | 2 |
| Polyvinylpyrrolidone | 4 |
| Sodium starch glycollate | 8 |

The tablets are formulated as described in part a. to yield tablets each weighing 200 mg.

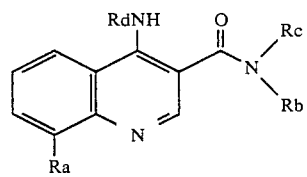

I

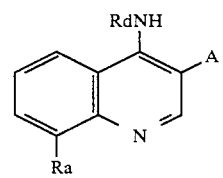

II

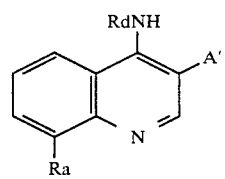

IIa

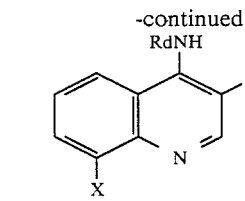

IIb

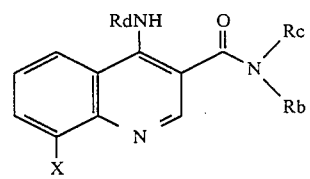

III

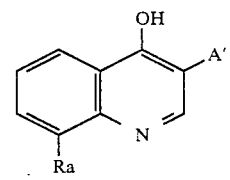

IV

What is claimed is:

1. A compound of formula I

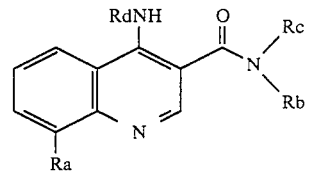

wherein
Ra is selected from the group consisting of (1–10C)alkyl, (3–10C)cycloalkyl, (4–10C)cycloalkylalkyl, (2–10C)alkenyl, (2–10C)alkynyl, (6–10C)aryl, (7–12C)arylalkyl, (1–10C)haloalkyl having one to five halo group(s) wherein the halo group(s) is selected from chloro and fluoro, (2–10C)hydroxyalkyl, (4–10C)hydroxycycloalkylalkyl, and thienyl wherein the thienyl is optionally substituted by (1–5C)alkyl;
Rb and Rc may be the same or different and are each independently selected from the group consisting of hydrogen, (1–10C)alkyl, (3–10C)cycloalkyl, (4–10C)cycloalkylalkyl, (2–10C)alkenyl, (2–10C)alkynyl, (2–10C)alkoxyalkyl, (2–10C)hydroxyalkyl, (3–10C)hydroxycycloalkyl, (4–10C)hydroxycycloalkylalkyl, (2–10C)haloalkyl having one to five halo group(s) wherein the halo group(s) is selected from chloro and fluoro, (3–6C)haloalkenyl having one to five halo group(s) wherein the halo group is selected from chloro and fluoro, phenyl and benzyl;
or Rb and Rc taken together form a (3–10C)alkylene and together with the nitrogen to which they are attached form a ring;
Rd is selected from the group consisting of hydrogen, (1–6C)alkyl and (1–6C)alkanoyl; and
pharmaceutically acceptable acid addition salts thereof.

2. A compound as claimed in claim 1 wherein
Ra is selected from a group consisting of (2–6C)alkyl, (3–7C)cycloalkyl, (4–7C)cycloalkylalkyl, (3–6C)alkenyl, (3–6C)alkynyl, (6–10C)aryl, benzyl, (3-6C)haloalkyl, (3-6C)hydroxyalkyl, (4-7C)hydroxycycloalkylalkyl, and 3-methyl-2-thienyl;

Rb and Rc are independently selected from a group consisting of hydrogen, (2-6C)alkyl, (3-7C)cycloalkyl, (4-7C)cycloalkylalkyl, (3-6C)alkenyl, (3-6C)alkynyl, (2-6C)alkoxyalkyl, (2-6C)haloalkyl, and (3-6C)haloalkenyl where the halo group(s) is on a carbon having a double bond;

Rd is selected from a group consisting of hydrogen and (2-4C)alkanoyl.

3. A compound as claimed in claim 2 wherein

Ra is selected from a group consisting of ethyl, propyl, butyl, pentyl, 3-pentynyl and 2-methylpropyl;

Rb is selected from a group consisting of propyl, 2-propenyl, cyclopropylmethyl, 2,2,2-trifluoroethyl, 2-chloro-2-propenyl, and 3,3-dichloro-2-propenyl;

Rc is hydrogen; and

Rd is hydrogen.

4. A compound as claimed in claim 1 selected from a group consisting of 4-amino-8-butylquinoline-3-[N-(2-propenyl)]carboxamide and 4-amino-8-butylquinoline-3-[N-propyl]carboxamide and the pharmaceutically acceptable salts thereof.

5. A compound as claimed in claim 1 wherein said compound is 4-amino-8-butylquinoline-3-[N-(2-propenyl)]carboxamide and the pharmaceutically acceptable salts thereof.

6. A compound as claimed in claim 1 wherein said compound is 4-amino-8-butylquinoline-3-[N-propyl]-carboxamide and the pharmaceutically acceptable salts thereof.

7. A pharmaceutical composition comprising a compound of any one of claims 1-6 or a pharmaceutically acceptable salt thereof in an amount sufficient to reduce anxiety in a living mammal in need of such treatment in association with a non-toxic pharmaceutically acceptable diluent or carrier.

8. A method of treating anxiety in a living mammal comprising administering to the mammal an anxiolytically effective amount of a compound of any one of claims 1-6 or a pharmaceutically acceptable salt thereof.

* * * * *